US012427302B2

(12) United States Patent
Engman

(10) Patent No.: US 12,427,302 B2
(45) Date of Patent: Sep. 30, 2025

(54) ON-DEMAND REMOTE DATA ACQUISITION AND PROGRAMMING IN A WEARABLE MEDICAL DEVICE

(71) Applicant: West Affum Holdings DAC., Dublin (IE)

(72) Inventor: Zoie R. Engman, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 461 days.

(21) Appl. No.: 17/689,671

(22) Filed: Mar. 8, 2022

(65) Prior Publication Data

US 2022/0280773 A1    Sep. 8, 2022

Related U.S. Application Data

(60) Provisional application No. 63/157,920, filed on Mar. 8, 2021.

(51) Int. Cl.
*A61N 1/00* (2006.01)
*A61B 5/00* (2006.01)
*A61N 1/04* (2006.01)
*A61N 1/372* (2006.01)
*A61N 1/39* (2006.01)

(52) U.S. Cl.
CPC ............ *A61N 1/046* (2013.01); *A61B 5/4836* (2013.01); *A61N 1/0484* (2013.01); *A61N 1/37282* (2013.01); *A61N 1/3904* (2017.08); *A61N 1/3925* (2013.01); *A61N 1/3968* (2013.01)

(58) Field of Classification Search
CPC ............................ A61N 1/046; A61N 1/39904
USPC ............................................................ 607/5
See application file for complete search history.

(56) References Cited

U.S. PATENT DOCUMENTS

| | | | |
|---|---|---|---|
| 3,724,355 | A | 4/1973 | Busch et al. |
| 3,724,455 | A | 4/1973 | Unger |
| 4,583,524 | A | 4/1986 | Hutchins |
| 4,619,265 | A | 10/1986 | Morgan et al. |

(Continued)

FOREIGN PATENT DOCUMENTS

| | | |
|---|---|---|
| DE | 102005060985 A1 | 6/2007 |
| EP | 2305110 A1 | 4/2011 |

(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

(Continued)

*Primary Examiner* — Nicole F Johnson
(74) *Attorney, Agent, or Firm* — POLSINELLI PC

(57) ABSTRACT

Technologies and implementations for a wearable healthcare system including a communication management module (CMM). The CMM may be configured to facilitate communication between a remote device and a wearable medical device (WMD), where the remote device may request second data from the WMD based upon first data provided by the CMM, request data periodically, request for on-demand data, stream live data, and/or may be capable of programming the WMD in a secure manner.

20 Claims, 10 Drawing Sheets

(56) References Cited

U.S. PATENT DOCUMENTS

| | | | |
|---|---|---|---|
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |

(56) References Cited

U.S. PATENT DOCUMENTS

| | | | |
|---|---|---|---|
| 2019/0030350 A1* | 1/2019 | Finch | A61B 5/742 |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |

FOREIGN PATENT DOCUMENTS

| | | |
|---|---|---|
| EP | 3380189 B1 | 10/2018 |
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011/146448 A1 | 11/2011 |
| WO | 2012064604 A1 | 5/2012 |
| WO | 2012/151160 A1 | 11/2012 |
| WO | 2015/056262 A1 | 4/2015 |

OTHER PUBLICATIONS

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Zoll, LifeVest, Proven protection from Sudden Cardiac Death, 2017, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

ON-DEMAND REMOTE DATA ACQUISITION AND PROGRAMMING IN A WEARABLE MEDICAL DEVICE

RELATED APPLICATION

This application claims benefit of priority to U.S. Provisional Patent Application Ser. No. 63/157,920, filed on Mar. 8, 2021, titled ON-DEMAND REMOTE DATA ACQUISITION AND PROGRAMMING IN A WEARABLE MEDICAL DEVICE, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be capable of determining various health related information about a person. For example, a healthcare device may be capable of determining health related information of an electrical activity of a person. The electrical activities of the person may include various electrical activities of various organs such as, but not limited to, brain activities, heart activities, skin moisture, gastrointestinal tract activities, breathing activities, etc.

The healthcare device may be included as part of a wearable system, where the wearable system may include a healthcare device configured to be worn by a person (e.g., a wearable medical device or a WMD) facilitating a more continuous monitoring and/or treatment of various health related issues of the person. For example, the WMD may be configured to monitor the electrical activities and/or treat potential health related issues of the heart. An example of a WMD for monitoring the electrical activities of the heart may be wearable cardioverter defibrillator (WCD).

The wearable system having the WMD may receive and store variety of information about the health of the person and any treatment that may have been administered to the person by the WMD. The variety of information may be informative to various people that may interact with the person (e.g., first responder, medical personnel, medical professional, etc.).

As may be appreciated, the WMD may be a relatively sophisticated device. In order to facilitate functionality of the WMD, the functionality of the WMD may be established by a variety of means. For Example, some of the functionality of the WMD may include establishing various software and/or hardware to facilitate the functionality of the WMD (i.e., installing and/or setting up the software and/or hardware). Additionally, once established, continued functionality of the WMD may include maintenance and/or repair of the WMD (e.g., software updates, changes in prescription, modifications to some functionality for the person, diagnostic processes, malfunction issues, and so forth).

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative wearable device systems and methods for managing on-demand communication of information regarding a wearable medical device (WMD). Example systems may include the WMD, a remote device, and a communication management module (CMM). Example systems may include the CMM configured to establish a communication link between the remote device and the WMD. The CMM may be configured to facilitate communication between the remote device and the WMD using the communication link, where the remote device may request second data from the WMD based upon first data provided by the CMM. The CMM may be configured to facilitate communication between the remote device and the WMD using the communication link, where the remote device may request data periodically. The CMM may be configured to facilitate communication between the remote device and the WMD using the communication link, where the remote device may request for on-demand data. The CMM may be configured to facilitate communication between the remote device and the WMD using the communication link, where the remote device may stream live data. The CMM may be configured to facilitate communication between the remote device and the WMD using the communication links, where the remote device may be capable of programming the WMD in a secure manner.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
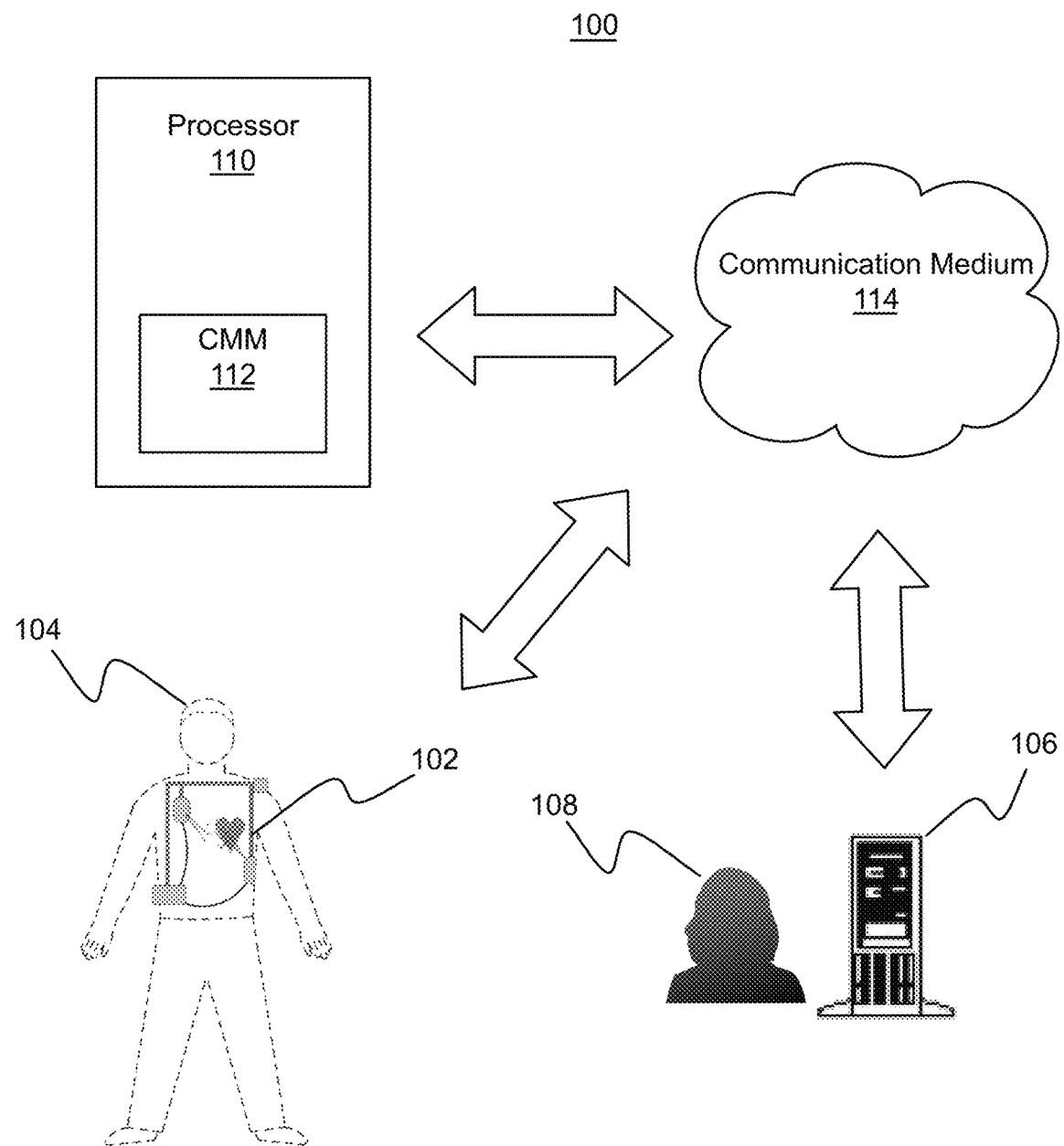
FIG. 1 illustrates a wearable medical device system in accordance with various embodiments.

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, and wearable device systems related to managing on-demand remote data acquisition and programming in a wearable medical device (WMD). Managing on-demand remote data acquisition and programming may include a communication management module (CMM).

Technology may provide an opportunity for remote management and delivery of healthcare. Recently, remote management and delivery of healthcare may have been dramatically increased due to a pandemic. For example, remote management and delivery of healthcare may include appointments with healthcare professionals and remote management of healthcare devices (e.g., a person may use a medical device at their residence). In the example of remote management of healthcare devices, a healthcare professional (e.g., a doctor located at a remote location) may find useful various information available from the healthcare device. For example, from the remote location, the doctor may receive information from the healthcare device that may cause the doctor to adjust medication of the person, where the information may be received from the healthcare device of the person in real time.

In some examples, the doctor may want to make some adjustments to the healthcare device itself. For example, the doctor may facilitate remote programming and/or adjusting of the healthcare device of the person. The remote programming and/or adjusting of the healthcare device of the person may be performed in real time.

For the purposes of providing a detailed description of the claimed subject matter, utilization of healthcare device may include a WMD and may be described as included in a wearable medical device system of the present disclosure. However, in various embodiments, the wearable medical device system of the present disclosure may include a variety of wearable devices such as, but not limited to, cardiac event monitors, Holter monitors, mobile cardiac telemetry (MCT) devices, brain activity monitors, wearable cardioverter defibrillators (WCDs), mobile devices (e.g., a mobile/smart phones), etc. Accordingly, the claimed subject matter is not limited in this respect.

Utilizing the example of a wearable medical device system including a WMD, the WMD may be configured to facilitate monitoring of electrical signals such as, but not limited to, monitoring of electrical signals from a heart of a person. For example, the WMD may be configured to monitor and treat potential issues with the heart (i.e., the person may have a health condition, where the electrical control system of the heart may malfunction causing the heart to beat irregularly or not at all). In some examples, these types of WMDs may include a defibrillator device. An example of a WMD, which may be configured to monitor and treat potential issues with the heart, may include a wearable cardioverter defibrillator (WCD). In the present disclosure, for the purposes of ease of understanding the various embodiments of the claimed subject matter, references may be made to a medical device such as, but not limited to, a WCD, where on-demand communication may be managed as disclosed in the various embodiments herein.

As part of the description of a WMD related to the activities of the heart, some issues with the heart may be briefly described. For example, some issues with the rate of the heartbeat may be generally referred to as an arrhythmia. Arrhythmia may be caused by many factors, but in general, an arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of an arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the WMD configured to be utilized to monitor and/or provide therapy to the heart, the medical device may be capable of monitoring the electrical signals of the heart and if necessary, administer therapy to the heart in the form of an electric shock. The WMD may monitor the electrical signals and provide the electric shock to the heart externally (i.e., through the surface of a body) via components commonly known as electrodes, where some of the electrodes may be monitoring electrodes and some of the electrodes may be therapy electrodes. The medical device may be in the form of a cardioverter defibrillator. The medical device may be included in a support structure configured to be worn by the person. In this example, the medical device may help facilitate monitoring the electrical activities of the heart and provide the electric shock to the heart in the VF condition. As a result, the medical device may help prevent Sudden Cardiac Death (SCD).

Before turning to the figures, some non-limiting example scenarios of utilization of various embodiments of wearable medical device systems may be described. In the non-limiting example scenarios, a person may have a heart condition, where the person may utilize a healthcare device, which could be wearable by the person such as, but not limited to, a wearable medical device (WMD). As mentioned, the WMD may be configured to facilitate monitoring and treatment of a heart condition of the person such as, but not limited to, a wearable cardioverter defibrillator (WCD). The WCD may include a support structure configured to be worn by the person such as, but not limited to, a garment (e.g., a vest). Included in the support structure of the WCD, a WCD monitor may include various components to facilitate the functionality of the WCD. A number of electrodes, monitoring electrodes and therapy electrodes, may be communicatively coupled with the WCD monitor. As the person wears the WCD, the WCD may receive various information from the person such as, but not limited to, electrical signals in the form of electrocardiogram (ECG) signals, and the ECG signals may be stored by the WCD.

In one example scenario, the WCD may be communicatively coupled with a communication medium such as, but not limited to, a network (e.g., the Internet). A remote device may be communicatively coupled with the communication medium, where the remote device may be utilized by a healthcare professional (e.g., a doctor). The remote device may be a computing device that may be utilized by the doctor such as, but not limited to, a server that may be configured to host a monitoring website that may facilitate a remote person such as a doctor or other health service provide to monitor the patient's status. The remote device can then display the data for the remote person. A communication management module (CMM) may be communicatively coupled with the communication medium. The CMM may be configured to establish a communication link between the remote device and the WCD via the Internet.

In this example scenario, the WCD may acquire and store data such as, but not limited to, ECG signals of the heart of the person. The CMM may communicate a request to receive the stored ECG data from the WCD. The CMM may transmit the received ECG data to the remote device. Once ECG data is received by the remote device, the remote device may be configured to detect potential issues with the ECG data (e.g., detecting potential issues with the heart rhythm). Based upon the received ECG data, the remote device may request additional data from the WCD (e.g., additional ECG data). The request may be communicated to the CMM, and the CMM may communicate a request for additional data from the WCD.

In some examples, the communication medium may be wireless, wired, or any combination thereof. Accordingly, the WCD and/or the remote device may be configured to include wireless and/or wired communication capabilities. Some examples of wireless communication capabilities may include capabilities such as, but not limited to, Wi-Fi, Bluetooth, Near-Field Communication (NFC), Radio-frequency identification (RFID), various IEEE 802 based wireless communications including Zigbee, cellular wireless communication, etc. Additionally, in some examples, the CMM may be hosted on a device having communication capabilities such as, but not limited to, a smartphone type device, a tablet type device, a smartwatch type device, and so forth). Alternatively, the CMM may be hosted by the WCD and/or the remote device.

In another non-limiting scenario, the wearable medical device system of the previous scenario may include capabilities of on-demand data acquisition and/or transfer. The on-demand data acquisition and/or transfer may be facilitated by the CMM. For example, the remote device may be configured to transmit a request to the WCD to acquire data being monitored by the WCD and transmit the acquired data to the remote device (e.g., a server hosting a remote monitoring website). The request for the data and the transmitting of the data may be facilitated by the CMM. For example, the remote device may be configured (e.g., by the remote person) to transmit the request to the WCD based on various configurable occurrences and/or triggers.

In some examples, configurable occurrences may include occurrences based on time of day and/or week (e.g., every Monday at 3:00 a.m.). In some examples, configurable occurrences may include occurrences based on events detected by the WCD. For example, the configurable occurrences may include an alert or an alarm for one or more specified single events or a recurring series of events. For example, the remote device may receive data from the WCD, facilitated by the CMM, where the received data may indicate a selected event or recurring series of events. Responsive to receiving the selected event or recurring series of events, the remote device may be configured to transmit the request to the WCD to acquire and store the data (e.g., ECG) and transmit the data to the remote device. Some examples of events may include the WCD may have detected a noise level above a predetermined threshold or an electrode off alert may have occurred (e.g., in a certain period of time). Review of the received data by the remote person may be facilitated at the remote device (e.g., user interface). The remote person may be provided the opportunity to assess and/or determine whether some corrective may be taken (e.g., the fit of the wearable device may be adjusted).

In some examples, configurable occurrences may include occurrences based on a trigger and/or an alarm that may be activated at the WCD (e.g., person wearing the wearable medical device and/or person at the WCD). The WCD may be include the capabilities to record and transmit patient data in response to the person triggering a button or other user interface when the person wearing the WCD is not feeling well (referred to herein as Patient Triggered Alerts). Accordingly, in one example, the remote device may be configured to automatically "follow-up" when the person wearing the WCD triggers the WCD device to record data in response to the Patient Trigger Alert.

In some examples, configurable occurrences may include occurrences based on equipment status. For example, a WCD may be configured to detect changes in status of one or more components utilized in the WCD, where the changes in the status may be included in a data transmitted to the remote device. One example of occurrences based on equipment status may include, where the WCD may be configured to detect identification data associated with various components utilized by the WCD (e.g., serial number, part number, catalog number, date of manufacture components, etc.). The identification data may be associated with the various components may change (i.e., new and/or modified equipment/components), which may be an indication of new and/or modified equipment/components (e.g., a replacement cable, sensors, batteries, etc.) utilized by the WCD. The detected identification data may be included in the data transmitted to the remote device. The remote device (e.g., a server hosting a remote monitoring website) or the CMM may be configured to detect the changes in the identification data, and in response, the remote device may transmit a request to the WCD to acquire and transmit data based on the received identification data back to the remote device for display (e.g., further information regarding the new and/or modified equipment/components.

In another example, the remote device or the CMM may be configured to detect changes in status of one or more components utilized in the WCD, where the changes in the status may be included in data received from the WCD. Responsive to the received data, the CMM or the remote device may transmit a request to the WCD to acquire data associated with the changes in status and transmit the data to the remote device, where the remote person may be provided an opportunity to review the changes.

In yet another example, the CMM and/or the remote system may be configured to flag when an equipment (e.g., the WCD) is delivered to the person including when the equipment has arrived (e.g., via shipment tracking information provided by the shipper). In this example, the CMM may be configured to initiate the storage/transfer of data from the equipment.

In some examples, the CMM may be configured to enable a user of the CMM to manually inform the CMM (e.g., via user interface) that the equipment has changed. In some examples, the CMM may be configured to prompt a user of the CMM to confirm that the equipment has changed. In some examples, the CMM may be configured to detect when a "profile" of an equipment has changed (e.g., settings of the WCD). In some examples, the CMM may be configured to detect when a new support structure is communicatively coupled to the CMM and/or included in the wearable medical device system.

In some examples, configurable occurrences may include occurrences based on detection by the WCD, the CMM, the remote device, and/or any combination thereof of crossing a threshold of the WCD such as, but not limited to, wear time (e.g., 200 hours of wear time).

In some examples, configurable occurrences may include occurrences based on triggers from a separate system. For example, the remote device may receive data from a "business system", where the business system may be configured to provide a variety of business related applications such as, but not limited to, managing inventory, billing, distribution, etc., involving the WCD. In one example, occurrences based on triggers from a separate system may include automatically storing data when the person may be due for a prescription renewal for the WCD, where the WCD may include prescriptions from the doctor. In another example, occurrences based on triggers from a separate system may include occurrences where there may be a receipt of a new equipment by the person that may not be able to be detected by the WCD. For example, the WCD may not have the capabilities to detect that the person is wearing a new support structure associated with the WCD. The information that the person is wearing the new support structure may be provided by a separate system to the remote device. Subsequently, the remoted device may transmit a request to acquire and transmit data regarding the new support structure, via the CMM, to the WCD.

In another non-limiting scenario, the wearable medical device system of the previous scenarios may include capabilities of an on-demand streaming process. For example, the wearable medical device system may be configured to enable the remote device to transmit a request that the CMM cause the WCD to stream data that may be acquired by the WCD to another remote device such as, but not limited to, a server hosting a remote monitoring website for display. For example, a remote device may transmit a request to the CMM to establish a streaming communication channel between the remote device and the WCD. As previously mentioned, the CMM may be hosted on a separate communication device that may be communicatively coupled with the WCD. Alternatively, the CMM may be hosted by the WCD, where the WCD may include various communication capabilities facilitating communicatively coupling with the remote device.

Continuing with the streaming example scenario, responsive to receiving the request, the CMM may transmit a request to the WCD to stream data to the CMM. In this example, the WCD may be configured to stream data to the CMM, which may transmit the data to the remote device via the established streaming communication channel. The remote device may be configured to facilitate viewing and/or interacting with the data at the remote device. The person utilizing the remoted device (e.g., doctor) may be provided the opportunity to view and/or interact with the streaming data. A wide variety of data may be streamed such as, but not limited to, ECG data, accelerometer data, algorithm decision data (e.g., rhythm determination data), algorithm state data (e.g., initial detection or superventricular tachycardia/SVT), device status data (e.g., electrode contact, battery status/capacity), event detection data (e.g., a record of a device state transition), and so forth. Accordingly, the claimed subject matter is not limited in this respect.

In yet another non-limiting scenario, the wearable medical device system of the previous scenarios may include capabilities of an on-demand programming process. For example, the wearable medical device system may be configured to enable the remote device to program the WCD (e.g., with settings, software updates, etc.).

In some examples, the remote device may be configured to transmit a request for a programming operation with the WCD, where the request may be transmitted via the CMM. The remote person may have the ability to transmit a request via the remote device (e.g., a server hosting a remote monitoring website) to the CMM. As previously described, the CMM may be hosted on a separate communication device (e.g., a smartphone, tablet, smartwatch, etc.), which may be communicatively coupled with the WCD. Alternatively, the CMM may be hosted on the WCD, where the WCD may have communication capabilities to be configured to communicate with the remote device. In this example, the CMM may be configured to facilitate the programming of the WCD. In various examples, the programming may include a wide variety of programs to facilitate operation of the WCD such as, but not limited to, one or more of the following operations:

the remote device may transmit a request to program the WCD
  the CMM may be configured to receive and acknowledge the request (i.e., accepts the request to program responsive to a remote user/person inputting information of the person wearing the WCD)

if the CMM receives and acknowledges the request (i.e., accepts the request), the remote device may be configured to authenticate the programming capabilities of the CMM responsive to the remote user (e.g., remote device user) inputting information regarding the person wearing the WCD (e.g., the patient), the CMM may be configured to confirm that the CMM and/or the WCD may be ready for programming the WCD may be configured to receive the programming and facilitate the programming the WCD may be configured to complete the programming once the programming is complete, the WCD may be configured to transmit success or failure of completion of the programming to the CMM the CMM may be configured to transmit the success or failure of the programming to the remote device the remote device may be configured de-authenticate the programming capabilities of the CMM the remote device may be configured to confirm that the programming operation was completed successfully (e.g., the remote device may be configured to display the success communication from the WCD and/or perform a verification or check process to confirm that programming operation was successful)

the remote device may be configured to transmit at notification to person wearing the WCD that the programming operation was successful, where the notification may be managed and facilitated by the CMM The operations described above may be managed and/or supervised by the person at the remote device via some of the examples described herein (e.g., on-demand streaming, user interface, etc.).

Turning to the Figures, FIG. 1 illustrates a wearable medical device system in accordance with various embodiments. In FIG. 1, a wearable medical device system 100 may include a wearable medical device (WMD) 102, which may be capable of being worn by a person 104 (e.g., a patient, who may be wearing the wearable medical device 102). As show, the wearable medical device system 100 may include a remote device 106 and a remote person 108 (e.g., a medical professional, who may be able to utilize the remote device 106, via some interface, for at least the various embodiments described herein). The wearable medical device system 100 may include a processor 110, where the processor 112 may include a communication management module (CMM) 112 configured to facilitate the various embodiments described herein. The communication module 112 may be hosted by various devices.

In FIG. 1, the wearable medical device system 100 may include a communication medium 114. The communication medium 114 may be a variety of communication mediums such as, but not limited to, the Internet. As shown, the WMD 102, the remote device 106, and the CMM 112 may be communicatively coupled with the communication medium 114.

In one example, the CMM 112 may be configured to a establish communication link between the remote device 106 and the WMD 102 via the communication medium 114. Once the communication link is established, the CMM 112 may be configured to communicate a first data from the WMD 102 to the remote device 106. Additionally, the CMM 112 may be configured to receive from the remote device 106 a request for a second data from the WMD 102, where the request for the second data may be based upon the communicated first data. The CMM 112 may cause the WMD 102 to acquire the second data.

In another example, once the communication is established between the remote device 106 and the WMD 102 via the communication medium 114, the CMM 112 may be configured to receive a request from the remote device 106, where the received request being periodic from the remote device 106. The CMM 112 may transmit instructions to the WMD 102 to acquire and store the requested data.

In another example, once the communication is established between the remote device 106 and the WMD 102 via the communication medium 114, the CMM 112 may be configured to receive a request for on-demand data from the remote device 106, where the on-demand data may be physiological data of the person 104 wearing the WMD 102. Responsive to the received request, the CMM 112 may be configured to at least one of stream the on-demand data from the WMD 102 to the remote device 106 and/or store the on-demand data.

In yet another example, once the communication is established between the remote device 106 and the WMD 102 via the communication medium 114, the CMM 112 may be configured to receive a request for data from the remote device 106. Responsive to the received request for data from the remote device 106, the CMM may be configured to stream live data from the WMD 102 to the remote device 106, where the remote person 108 may view via a variety of interface types.

In yet another example, once the communication is established between the remote device 106 and the WMD 102 via the communication medium 114, the CMM 112 may be configured to receive a request to program the WMD 102 from the remote device 106. Responsive to the received request to program the WMD 102, the CMM 112 may be configured to facilitate remote programming of the WMD 102 in a secure manner. In one example, the remote programming may be performed by the remote person 108 utilizing the remote device 106. In another example, the remote programming may be performed by the remote device 106 as part of an automated process. In yet another example, the programming may be performed by the CMM 112 as requested by the remote device 106.

In FIG. 1, the processor 110 having the CMM 112 may be included in a wide variety of communication devices such as, but not limited to, a smartphone, smartwatch, tablet, a WMD having communication capabilities, and so forth. Correspondingly, the CMM 112 may be hosted by a wide variety of devices. Accordingly, the claimed subject matter is not limited in this respect.

In FIG. 1, the remote device 106 may be a wide variety of devices such as, but not limited to, a computing device, a server, a medical professional device, and so forth. Correspondingly, the remote person 108 may be a wide variety of people such as, but not limited to, a medical professional (e.g., a doctor, a nurse, etc.), a programming professional (e.g., software engineer, device manufacturer, etc.), and so forth. Accordingly, the claimed subject matter is not limited in this respect.

As described above in some of the non-limiting scenarios, the WMD 102 may be a variety of wearable medical devices such as, but not limited to, a wearable cardioverter defibrillator (WCD), cardiac event monitors, Holter monitors, mobile cardiac telemetry (MCT) devices, brain activity monitors, and so forth. Accordingly, claimed subject matter is not limited in this respect.

As mentioned, the communication medium 114 may include a wide variety of communication mediums such as, but not limited to, the Internet, personal area networks (PAN), local area networks (LAN), wireless local area networks (WLAN), campus area networks (CAN), metropolitan area networks (MAN), wide area networks (WAN), storage-area networks (SAN), system-area networks, passive optical local area networks (POLAN), enterprise private networks (EPN), virtual private networks (VPN), and so forth. Accordingly, the claimed subject matter is not limited in this respect.

Correspondingly, the various communication methodologies may be utilized such as, but not limited to, wired communication methodologies, wireless communication technologies including wireless protocols such as, but not limited to, Wi-Fi, Bluetooth, Near-Field Communication, Radio-frequency identification (RFID), various IEEE 802 based wireless communication including Zigbee, cellular wireless communication, and so forth. Accordingly, the claimed subject matter is not limited in this respect.

Figure 2:
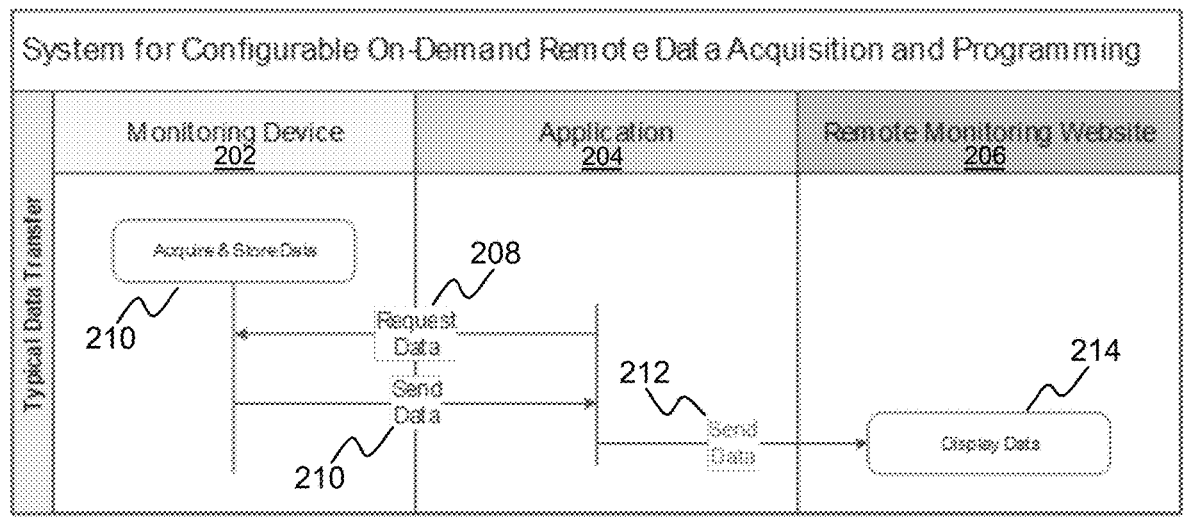
FIG. 2 illustrates an example of a data transfer process in accordance with one more embodiments.

FIG. 2 illustrates an example of a data transfer process in accordance with one more embodiments. In FIG. 2, a data transfer process 200 may include a monitoring device 202 (e.g., a wearable medical device), an application 204 (e.g., a CMM), and a remote monitoring device 206 (e.g., a remote device). The monitoring device 202, the application 204, and the remoted monitoring device 206 may be part of a wearable medical device system as described herein, and accordingly, may be communicatively coupled with a communication medium.

In FIG. 2, the data transfer process 200 may include the application 204 transmitting a request for data 208 to the monitoring device 202. Responsive to the request for data 208, the monitoring device 202 may acquire and store the data 210. The monitoring device 202 may send the data 212 to the application 204. The application 204 may send the data 212 to the remote monitoring device 206, where remote monitoring device 206 may be configured to display the data 214 for a remote person. As a result, data transfer process may be facilitated in accordance with one more embodiments.

Figure 3:
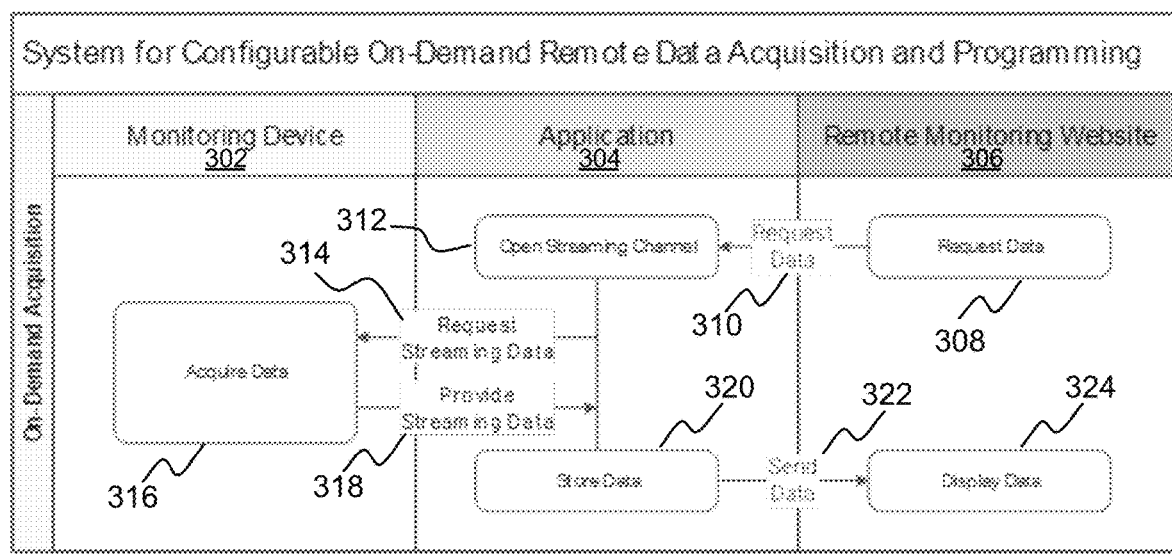
FIG. 3 illustrates on-demand acquisition process in accordance with one or more embodiments.

FIG. 3 illustrates on-demand acquisition process in accordance with one or more embodiments. In FIG. 3, an on-demand acquisition process 300 may include a monitoring device 302 (e.g., a wearable medical device), an application 304 (e.g., a CMM), and a remote monitoring website 306 (e.g., a website that may be accessible by one or more remote devices). The monitoring device 302, the application 304, and the remoted monitoring website 306 may be part of a wearable medical device system as described herein, and accordingly, may be communicatively coupled with a communication medium.

In FIG. 3, the on-demand acquisition process 300 may include a request for data 308 at the remote monitoring website 306, which may be facilitated by an interface utilized by a remote person. Responsive to the request for data 308, remote monitoring website 306 may facilitate transmission of a request for data 310. Responsive to receiving the request for data 310 from the remote monitoring website 306, the application 304 may open a streaming channel 312. The application 304 may transmit a request for streaming data 314 to the monitoring device 302. Responsive to receiving the request for streaming data 314, the monitoring device 302 may acquire data 316. The monitoring device 302 may be configured to provide streaming data 318 to application 304, where the application may be configured to store the data 320. The application 304 may be configured to send data 322 to the remote monitoring website 306, where the remote monitoring website 306 may be configured to display the data 324 (e.g., an interface to facilitate utilization by the remote person). As a result, on-demand acquisition process may be facilitated in accordance with one or more embodiments.

Figure 4:
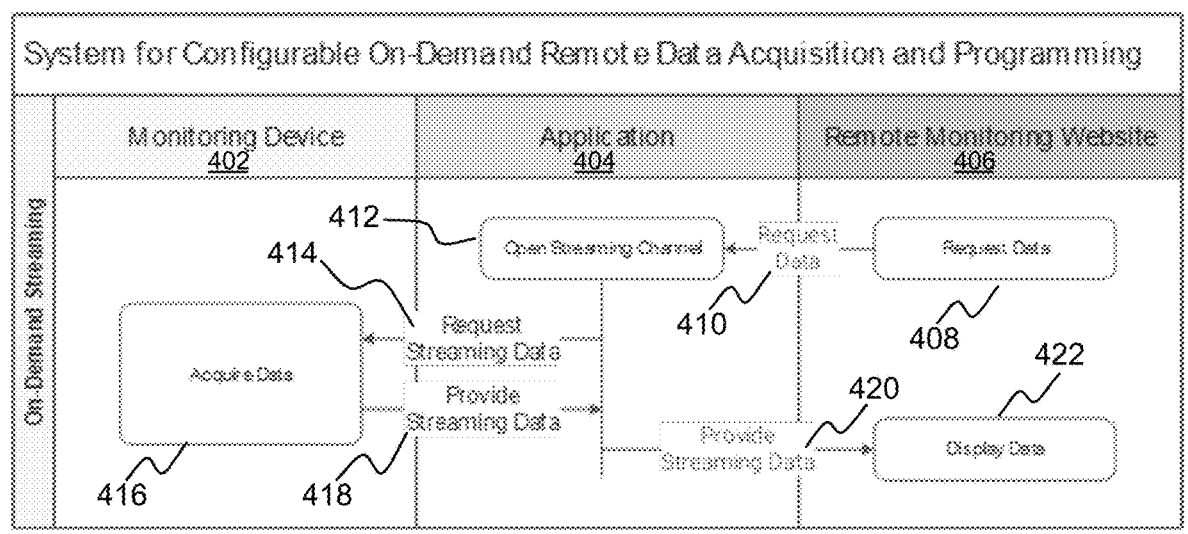
FIG. 4 illustrates on-demand streaming process in accordance with one or more embodiments.

FIG. 4 illustrates on-demand streaming process in accordance with one or more embodiments. In FIG. 4, an on-demand acquisition process 400 may include a monitoring device 402 (e.g., a wearable medical device), an application 404 (e.g., a CMM), and a remote monitoring website 406 (e.g., a website that may be accessible by one or more remote devices). The monitoring device 402, the application 404, and the remoted monitoring website 406 may be part of a wearable medical device system as described herein, and accordingly, may be communicatively coupled with a communication medium.

In FIG. 4, the on-demand acquisition process 300 may include a request for data 408 at the remote monitoring website 406, which may be facilitated by an interface utilized by a remote person. Responsive to the request for data 408, remote monitoring website 406 may facilitate transmission of a request for data 410. Responsive to receiving the request for data 410 from the remote monitoring website 406, the application 404 may open a streaming channel 412. The application 404 may transmit a request for streaming data 414 to the monitoring device 402. Responsive to receiving the request for streaming data 414, the monitoring device 402 may acquire data 416. The monitoring device 402 may be configured to provide streaming data 418 to application 404, where the application may be configured to provide the streaming data 420 in real-time to the remote monitoring website 406, where the remote monitoring website 406 may be configured to display the data 422 (e.g., an interface to facilitate utilization by the remote person). As a result, on-demand streaming process may be facilitated in accordance with one or more embodiments.

Figure 5:
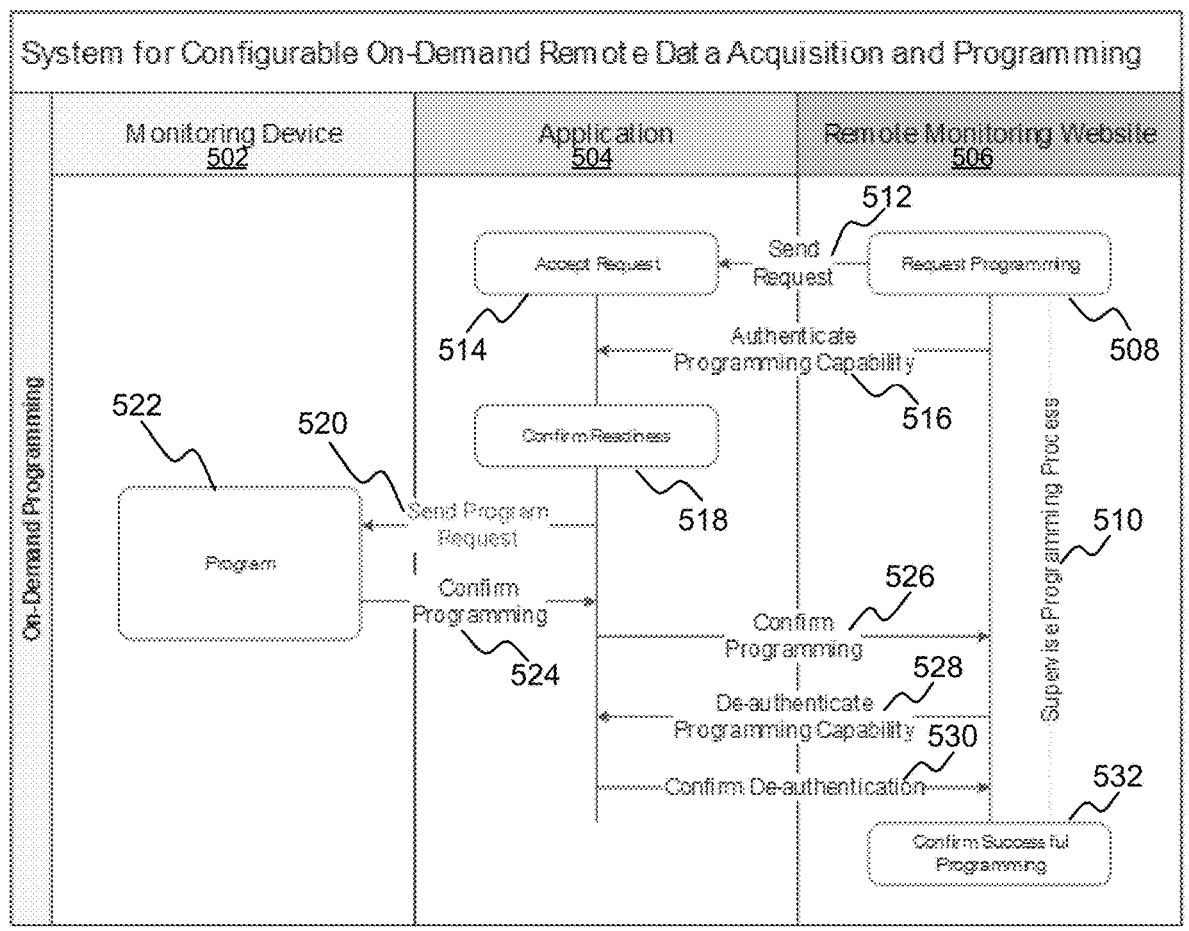
FIG. 5 illustrates on-demand programming process in accordance with one or more embodiments.

FIG. 5 illustrates on-demand programming process in accordance with one or more embodiments. In FIG. 5, an on-demand programming process 500 may include a monitoring device 502 (e.g., a wearable medical device), an application 504 (e.g., a CMM), and a remote monitoring website 506 (e.g., a website that may be accessible by one or more remote devices). The monitoring device 502, the application 504, and the remoted monitoring website 506 may be part of a wearable medical device system as described herein, and accordingly, may be communicatively coupled with a communication medium.

In FIG. 5, the on-demand programming process 500 may include a request for programming 508 at the remote monitoring website 506, which may be facilitated by an interface utilized by a remote person. The remote monitoring website 506 may include a supervise programming process 510, which may facilitate the on-demand programming of the monitoring device 502 by one or more remote devices and/or one or more remote persons. The remote monitoring website 506 may send the request 512 to the application 504. The application 504 may be configured to accept the request 514. Responsive to the application 504 accepting the request 514, the remote monitoring website 506 may authenticate programming capability 516 of the application 504. If the remote monitoring website 506 authenticates the programming capability 516 of the application 504, the application 504 may confirm readiness 518, where the confirmation may be responsive to a user input by the person wearing the monitoring device 502 (e.g., similar to an update to a computing device). Once confirmed readiness 518 by the application 504, the application 504 may send the program request 520 to the monitoring device 502. Responsive to receiving the send the program request 520, the monitoring device 502 may be configured to program 522 one or more various components included in the monitoring device 502 including completing the programming. The monitoring device 502 may be configured to transmit a confirm of the programming 524 to the application 504. The confirm of the programming 524 may include confirmation of success or failure of the programming communicated to the application 504. The application 504 may transmit the confirm of the programming 526 to the remote monitoring website 506. Responsive to receiving the confirm of the programming 526 from the application, the remote monitoring website may transmit instructions to de-authenticate programming capability 528 of the application 504. The application 504 may communicate confirm of de-authentication 530 to the remote monitoring website 506. The remote monitoring website 506 may be configured to communicate confirm successful programming 532, where the confirm successful programming 532 may include performing a verification and/or a checking process to confirm that the programming operation was successful. In addition to and/or alternatively, the confirm successful programming 532 may include utilization of an interface (e.g., user interface and/or display), which may be utilized by the remote person. As a result, on-demand programming process may be facilitated in accordance with one or more embodiments.

Figure 6:
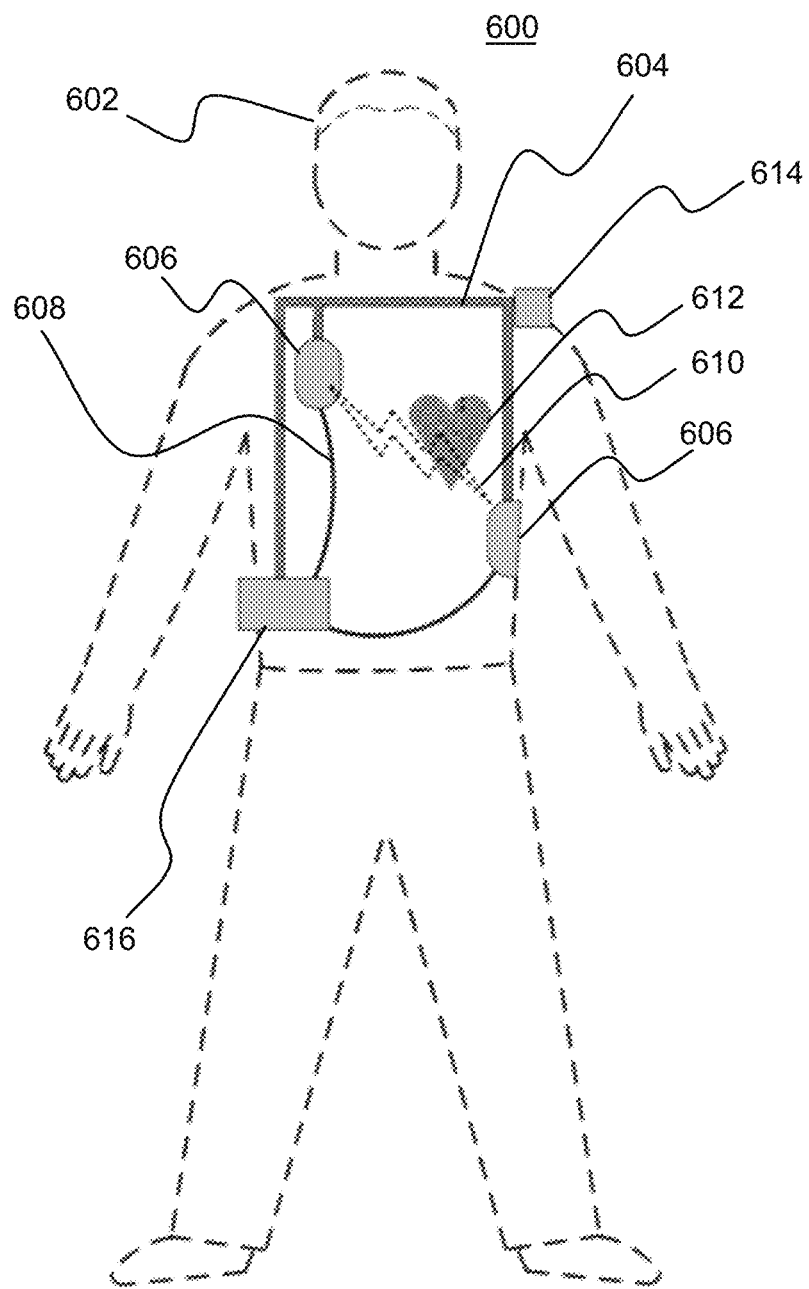
FIG. 6 illustrates a wearable medical device (WMD) in accordance with various embodiments.

FIG. 6 illustrates a wearable medical device (WMD) in accordance with various embodiments. In FIG. 6, a WMD 600 may be configured by a person 602. The person 602 may also be referred to a patient and/or wearer since the person 602 may be wearing various components of the WMD 600. The person 602 may be ambulatory, which means that, while wearing the wearable portion of the WMD 600, the person 602 may walk around and may not necessarily be bed ridden. While person 602 may be considered to be also a "user" of the WMD 600, this is not a requirement. For example, a user of the WMD 600 may also be a clinician such as, but not limited to, a doctor, nurse, emergency medical technician (EMT) and/or other similarly tasked individual or group of individuals. In some examples, a user may even be a bystander. The particular context of these and other related terms within this description should be interpreted accordingly.

Shown in FIG. 6, the WMD 600 may include a support structure 604 that may be wearable by the person 602. Accordingly, the support structure 604 may be configured to be worn by the person 602 for at least several hours per day, for at least several days, and/or for a few months. It should be understood that the support structure 604 is shown generically in FIG. 6 and may be partially conceptual. Accordingly, the WMD 600 may be shown to provide merely illustrative concepts about the support structure 604 and is not to be construed as limiting as to the manner of the implementation of the support structure 604 is implemented or the manner of how the support structure 604 may be worn.

It should be appreciated that the support structure 604 may be implemented in a wide variety of manners. For example, the support structure 604 may be implemented as a single component or a combination of multiple components. In some examples, the support structure 604 may include a vest, a half-vest, a garment, and so forth. In such examples, the support structure 604 may be worn similarly to analogous articles of clothing. In some examples, the support structure 604 may include a harness, one or more belts, and/or straps, and so forth. In such examples, the support structure 604 may be configured to be worn by the person 602 around the torso, hips, over the shoulder, and so forth. In some examples, the support structure 604 may include a container or housing, which may be water resistant/proof. In such examples, the support structure 604 may be configured to be worn by being attached to the body of the person 602 by adhesive material as shown in some examples described in U.S. Pat. No. 8,024,037. The support structure 604 may be implemented as some examples described for support structures of US Pat. App. No. US2017/0056682, which is incorporated herein by reference. As may be appreciated, the person skilled in the relevant art will recognize that additional components of the WMD 600 may be included in a housing of the support structure 604 instead of being attached externally to the support structure as may be described in the US2017/0056682 document.

In FIG. 6, the WMD 600 may be described an external defibrillator (e.g., wearable cardioverter defibrillator or WCD), which may include a housing and an energy storage module within the housing. As such, in the context of a WCD, the WMD 600 may be also known as a main electronics module. The energy storage module may be configured to store an electrical charge. Other components can cause at least some of the stored electrical charge to be discharged via electrodes through the person 602 to facilitate delivery of one or more defibrillation shocks through the person 602. Additional details of the WMD 600 may be described in additional sections of the present disclosure.

Turning now to some of the details in FIG. 6, the WMD 600 may include defibrillation electrodes 606, which may be electrically coupled to the WMD 600 via electrode leads 608. The defibrillation electrodes 606 may be configured to be worn by the person 604 in a variety of manners. For example, the WMD 600 and the defibrillation electrodes 606 may be electrically coupled to the support structure 604 either directly or indirectly. That is, the support structure 604 may be configured to be worn by the person 602 while maintaining at least one of defibrillation electrodes 606 may be in contact on the body of person 602. The contact on the body of the person 602 may be maintained, while the person 602 may be moving around. Accordingly, at least one of the defibrillation electrodes 606 may be maintained on the body of the person 602 by being attached to the skin of person 602 (e.g., pressed against the skin directly or through garments). In some examples, the defibrillation electrodes 606 may not be pressed against the skin of the person 602 (i.e., not in direct contact), but may be or become biased as if pressed against the skin of the person 602 to facilitate sensing a condition that may merit intervention by the WMD 600. Additionally, various components of WMD 600 may be considered included/coupled to support structure 604 directly and/or indirectly via at least one of defibrillation electrodes 606.

In FIG. 6, when the defibrillation electrodes 606 make good electrical contact with the body of the person 602, the WCD 600 may be capable of administering, via the defibrillation electrodes 606, a brief, strong electric pulse 610 through the body of the person 602. The electric pulse 610, which may be also known as a shock, a defibrillation shock, a therapy, an electrotherapy, a therapy shock, and so forth. The electric pulse 610 may be intended to go through and restart the heart 612 of the person 602, which may be an effort to save the life of person 602. The electric pulse 610 may include one or more pacing pulses of lesser electrical magnitude to facilitate pacing of the heart 612 as needed.

In some examples, the WMD 600 may initiate defibrillation, or hold-off defibrillation, based on a variety of inputs, where an electrocardiogram (ECG) signal may be included as one or more variety of inputs.

The WMD 600 shown in FIG. 6, may be configured to obtain data from the person 602. In one example, the WMD 600 may include at least an outside monitoring device 614, which may be configured to facilitate the obtaining of the data (i.e., collecting the data). The outside monitoring device 614 may be referred to as an "outside" device because it could be provided as a standalone device (i.e., not included within the housing of a WMD monitor 616. The WMD monitor 616 may include various components to facilitate the functionality of the WMD 600 (e.g., defibrillator). Some of the various components may be described with respect to FIG. 10.

The outside monitoring device 614 may be configured to sense or monitor at least one local parameter. A local parameter may be a parameter of the person 602, a parameter of the WMD 600, and/or or a parameter of the environment, as may be described in other sections of the present disclosure. For some of these parameters, outside monitoring device 614 may include one or more sensors or transducers to facilitate sensing or monitoring at least one local parameter. Each one of such sensors may be configured to sense a parameter of the person 602 and to provide an input responsive to the sensed or monitored parameter. In some examples, the input may be quantitative such as, but not limited to values of a sensed parameter. In some examples, the input may be qualitative such as, but not limited to, informing whether or not a threshold is crossed. Sometimes these inputs about person 602 may also be referred to as physiological inputs and/or patient inputs. As may be appreciated, a sensor can be construed more broadly as encompassing many individual sensors.

Optionally, outside monitoring device 614 may be physically coupled to the support structure 604. Additionally, outside monitoring device 614 may be communicatively coupled with other components that may be coupled to the support structure 604. Such communication may be implemented by a communication module, as will be deemed applicable by a person skilled in the relevant art in view of the present disclosure.

In some examples, one or more of the components of the WMD 600 may be customized for the person 602. The customization may include a number of aspects. In one example, the support structure 604 may be tailored to the body of the person 602. In another example, a baseline physiological parameters of the person 602 may be measured such as, but not limited to, the heart rate of the person 602 while resting, while walking, motion detector outputs while walking, and so forth. The measured values of such baseline physiological parameters may be utilized to facilitate customization of the WMD 600, which may facilitate a more accurate diagnoses for bodies that may differ from one person to another. The physiological parameter values may be stored in a storage medium of the WMD 600. Additionally, a programming interface may be included according to some embodiments, which may be configured to receive such measured values of physiological parameters. The programming interface may be configured to acquire and/or input and/or store in the WMD 600 variety of data including the physiological parameters.

Figure 7:
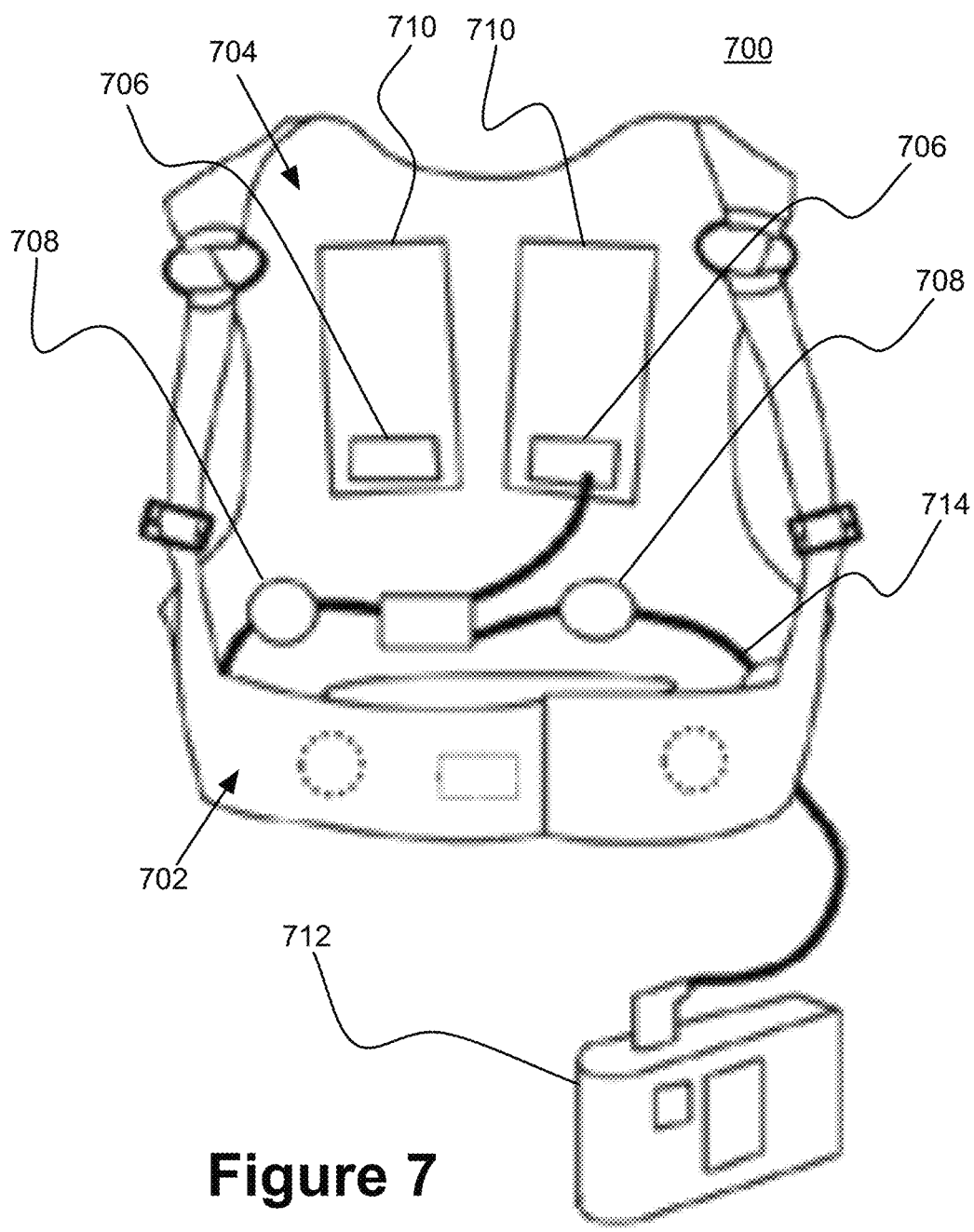
FIG. 7 illustrates a wearable medical device (WMD), in accordance with various embodiments.

FIG. 7 illustrates a wearable medical device (WMD), in accordance with various embodiments. In FIG. 7, a WMD may be configured to facilitate monitoring and treatment of a person's heart such as, but not limited to, a wearable cardioverter defibrillator (WCD) 700. The WCD 700 may be in the form of a clothing configured to be worn by a user such as, but not limited to, a vest type. Accordingly, the WCD 700 may have a front side 702 and a back side 704 forming the vest type WCD 700 as shown. Additionally, the WCD 700 may include one or more electrodes configured to defibrillate the person's heart, defibrillator electrodes (therapy electrodes 706) and one or more electrodes configured to detect and measure the person's electrocardiogram (ECG), monitor electrodes 708.

The WCD 700 may be configured to be worn by the person to facilitate maintenance of the therapy electrodes 706 and the monitor electrodes 708 on the body of the person. For example, therapy electrodes 706 may be included in pockets 710. In one example, the inside of pockets 710 can be made of loose netting to facilitate contact of the therapy electrodes 706 on the back of the person and may include assistance of conductive fluid that may have been deployed for the therapy electrodes 706. Additionally, the monitor electrodes 708 may be maintained in positions that may surround the torso of the person torso, which may facilitate sensing ECG signals and/or the impedance of the person.

In some examples, the ECG signals may include too much electrical noise to be useful. In order to address the electrical noise, multiple monitor electrodes 708 may be utilized to sense the ECG signals and may be processed. These options are different vectors for sensing the ECG signal, as described now in more detail.

It should be appreciated after review of this disclosure that the locations of the therapy electrodes 706 may be shown in various configurations such as, but not limited to, one front and one back, across a chest, across a back, etc. to facilitate defibrillation, and accordingly, the locations of the therapy electrodes 706 and/or the monitor electrodes 708 in FIG. 7 may be for illustrative purposes to show that there may be some electrodes to facilitate operation of the WCD 700. Additionally, for the purposes of the detailed description, references may be made to "an electrode", which may be any one of electrodes (therapy electrodes 706 and/or monitor electrodes 708) to provide the functionality of the WCD 700.

Continuing to refer FIG. 7, the WCD 700 may include a WCD monitor 712. In the example shown in FIG. 7, the WCD monitor 712 may be communicatively coupled to the therapy electrodes 706 and/or monitor electrodes 708 via one or more wires 714. However, in some other examples, the WCD monitor 712 may be integrated with the WCD such as, but not limited to, the back side 704. The WCD monitor 712 may include various components to facilitate the functionality of the WCD 700 (i.e., monitor and defibrillate the person's heart) such as, but not limited to, a processor, memory, power supply (e.g., battery), a display, etc. Some of these components may be described in further detail later in the disclosure.

It should be appreciated that the example WCD 700 shown in FIG. 7 may be in the form of a vest. However, the WCD 700 may be in the form of a wide variety of clothing such as, but not limited to, a jacket, a t-shirt, a dress shirt, a belt, a blouse, a coat, and any combination thereof. Accordingly, the components of the WCD 700 may be integrated with a wide variety of wearable clothing.

Figure 8:
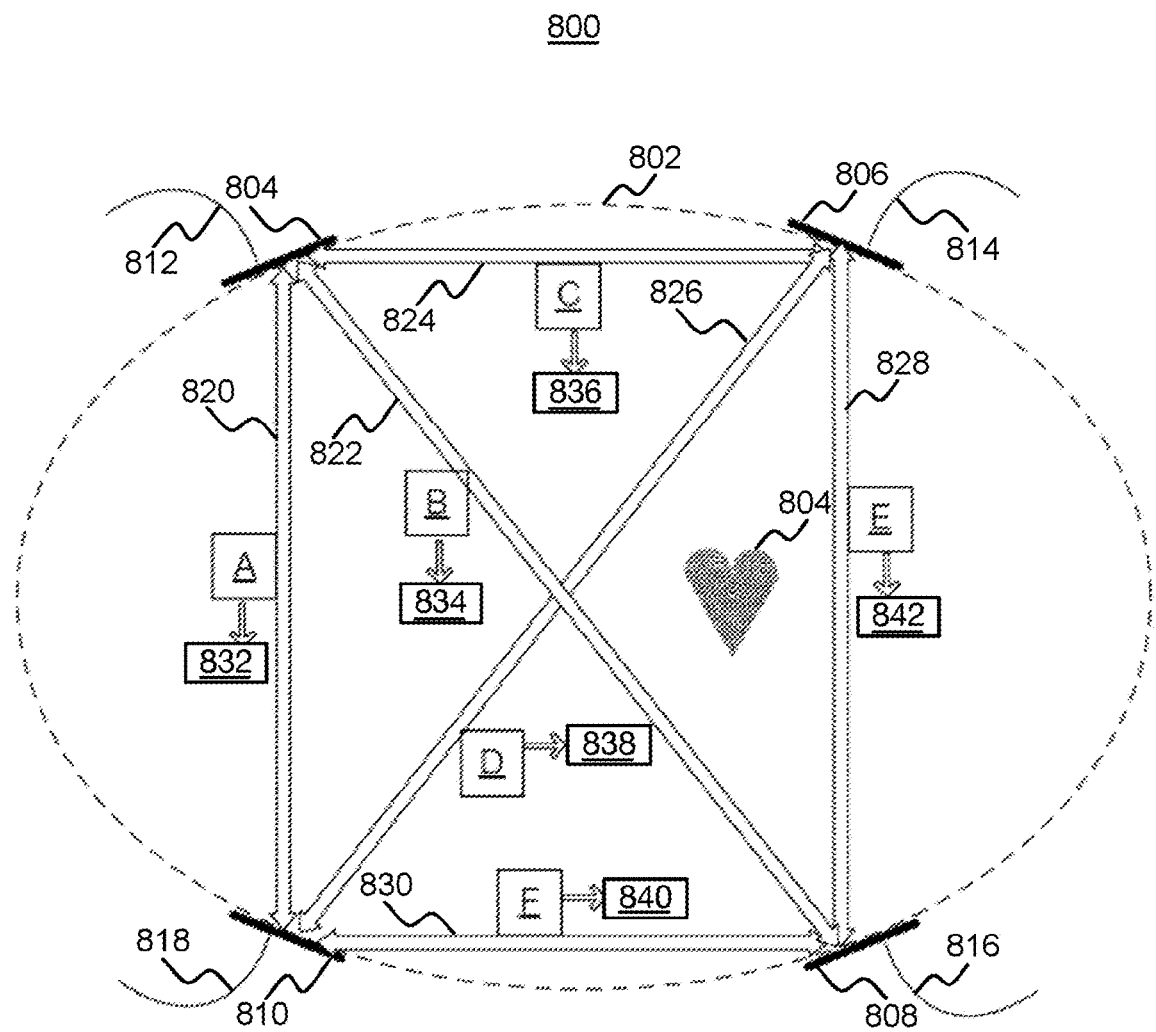
FIG. 8 illustrates a conceptual diagram for illustrating utilization of multiple electrodes of a WCD system that may be used for sensing ECG signals along different vectors according to various embodiments.

FIG. 8 illustrates a conceptual diagram for illustrating utilization of multiple electrodes of a WCD system that may be used for sensing ECG signals along different vectors according to various embodiments. In FIG. 8, the sizes/shapes/positions of the torso, electrodes, and heart may be approximations and not to scale. In FIG. 8, a WCD system 800 may include a section of a person 802 having a heart 804 may be shown. In FIG. 8, the person 802 may be viewed from the top, the person 802 may be facing downwards, and the plane of FIG. 8 may intersect the person 802 at the torso of the person 802.

Shown in FIG. 8, four ECG sensing electrodes 804, 806, 808, and 810 may be maintained on the torso of person 802 and may include wire leads 812, 814, 816, and 818 respectively. In FIG. 8, the four ECG sensing electrodes 804, 806, 808, and 810 may be located to substantially surround the torso of the person 802 similar to the monitor electrodes 708 shown in FIG. 7.

Any pair of the four ECG sensing electrodes 804, 806, 808, and 810 may define a vector, along which an ECG signal may be sensed and/or measured. Accordingly, the four ECG sensing electrodes 804, 806, 808, and 810 may define six vectors 820, 822, 824, 826, 828, and 830. Accordingly, FIG. 8 may illustrate a multi-vector embodiment.

In FIG. 8, the vectors 820, 822, 824, 826, 828, and 830 may define channels A, B, C, D, E, and F, respectively. The channels A, B, C, D, E, and F may be utilized to sense and/or measure ECG signals 832, 834, 836, 838, 840, and 842 from channels A, B, C, D, E, and F, respectively. Each of the channels A, B, C, D, E, and F may include pairings of the wire leads 812, 814, 816, and 818.

Shown in FIG. 8, the ECG sensing electrodes 804, 806, 808, and 810 may be illustrated as being on the same plane for simplicity and ease of understanding but may not be on the same place. Accordingly, the vectors 820, 822, 824, 826, 828, and 830 may not be on the same plane.

In some examples, in order to make the shock/no-shock determination, a WCD may determine which of ECG signals 832, 834, 836, 838, 840, and 842 may be best for rhythm analysis and interpretation. For example, ECG signals that have the most noise may be ignored, discarded, and/or not considered, while leaving the remaining ECG signals as candidates for making the shock/no shock determination.

In some examples, the vectors 820, 822, 824, 826, 828, and 830 may be aggregated to make a shock/no shock decision, and/or to determine the heart rate and/or QRS widths of the person 802. Some examples aggregation may be implemented as disclosed in U.S. Pat. No. 9,757,581 issued Sep. 12, 2017, entitled "WEARABLE CARDIOVERTER DEFIBRILLATOR COMPONENTS MAKING AGGREGATE SHOCK/NO SHOCK DETERMINATION FROM TWO OR MORE ECG SIGNALS", which is incorporated herein by reference.

Because a WCD may be worn by an ambulatory person (i.e., ambulatory patients), movement by the person may cause changes at the electrode-skin interface, which may introduce noise in an ECG signal. The noise introduced in the ECG signal may negatively affect the processing and interpretation of the ECG signal.

In some examples, the WCD 800 device may utilize the four ECG sensing electrodes 804, 806, 808, and 810, which may generate six differential ECG vectors 820, 822, 824, 826, 828, and 830. When the person 802 wearing the WCD 800 may be moving, some of the ECG sensing electrodes 804, 806, 808, and 810 may move more than others which may cause some of the ECG vectors 820, 822, 824, 826, 828, and 830 having more noise than other ECG vectors. In some examples, different assessment methods may be utilized on the ECG vectors 820, 822, 824, 826, 828, and 830. If the assessments for one of the ECG vectors 820, 822, 824, 826, 828, and 830 have similar results, the one ECG vector may be determined to be reliable. The ECG vectors determined to be reliable may be utilized in a rhythm analysis, which may increase accuracy.

In some examples, a single ECG vector may be utilized, where different assessment methods can be used. For example, an assessment method may include utilizing the single ECG vector, where portions of the ECG signal, which may have been determined to be reliable, may be utilized in the rhythm analysis. In another example, the WCD 800 may be configured to prompt the person 802 to reduce activity if the number of ECG portions that may be determined to be unreliable exceeds a predetermined threshold, which may cause a reduction on the amount of noise that may be generated by the movement of the person and may increase the number of ECG portions that may be determined to be reliable.

Figure 9:
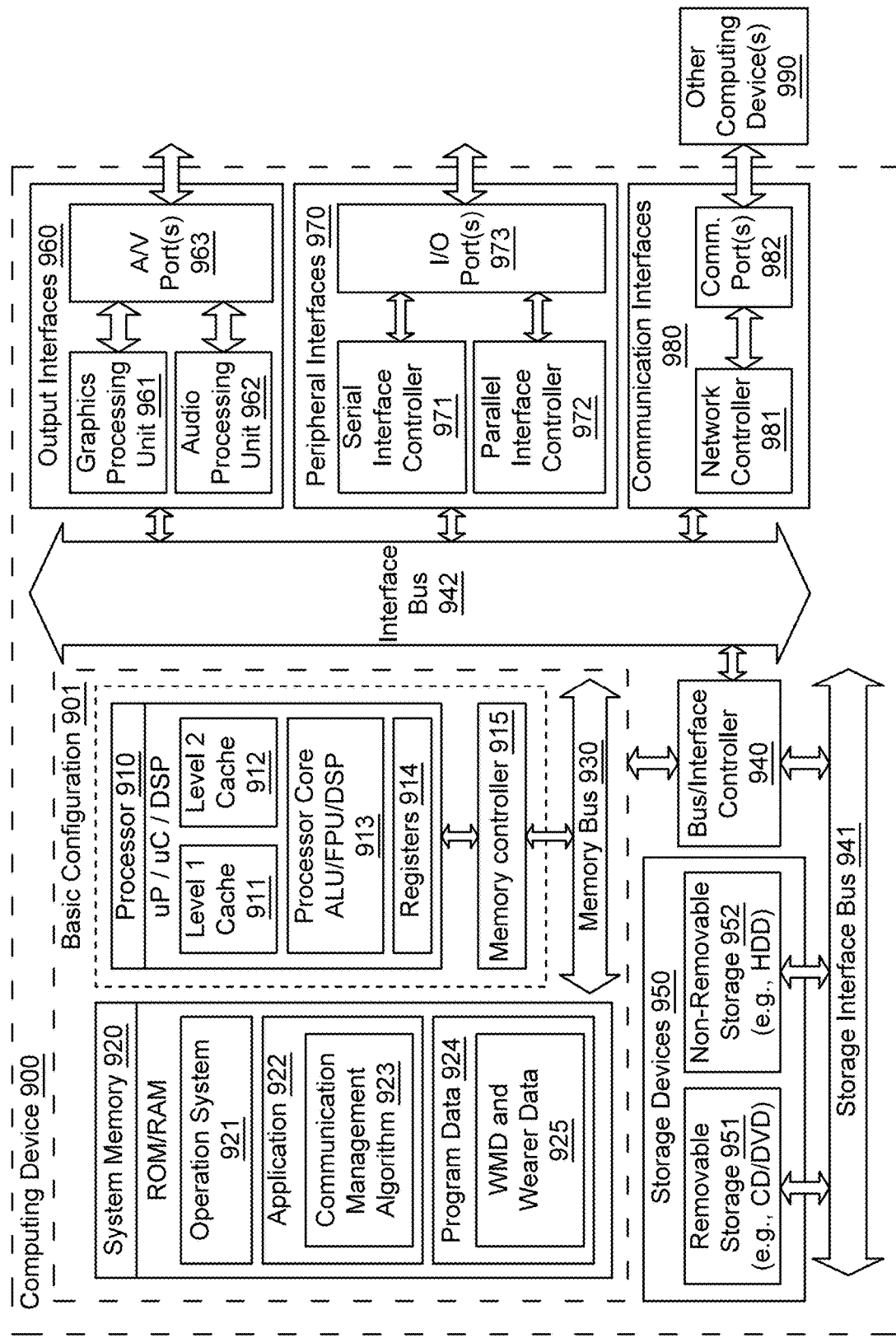
FIG. 9 is a block diagram illustrating an example computing device, such as might be embodied by a person skilled in the art, which is arranged in accordance with at least some embodiments of the present disclosure.

FIG. 9 is a block diagram illustrating an example computing device 900, such as might be embodied by a person skilled in the art, which is arranged in accordance with at least some embodiments of the present disclosure. In one example configuration, computing device 900 may include one or more processors 910 and system memory 920. A memory bus 930 may be used for communicating between the processor 910 and the system memory 920.

Depending on the desired configuration, processor 910 may be of any type including but not limited to a microprocessor (μP), a microcontroller (μC), a digital signal processor (DSP), or any combination thereof. Processor 910 may include one or more levels of caching, such as a level one cache 911 and a level two cache 912, a processor core 913, and registers 914. The processor core 913 may include an arithmetic logic unit (ALU), a floating point unit (FPU), a digital signal processing core (DSP Core), or any combination thereof. A memory controller 915 may also be used with the processor 910, or in some implementations the memory controller 915 may be an internal part of the processor 910.

Depending on the desired configuration, the system memory 920 may be of any type including but not limited to volatile memory (such as RAM), non-volatile memory (such as ROM, flash memory, etc.) or any combination thereof. System memory 920 may include an operating system 921, one or more applications 922, and program data 924. Application 922 may include communication management algorithm 923 that is arranged to perform the functions as described herein including the functional blocks and/or actions described. Program Data 924 may include, among other information described, WMD and wearer data 925 (e.g., physiological information regarding the person wearing the WMD) for use with the communication management algorithm 923. In some example embodiments, application 922 may be arranged to operate with program data 924 on an operating system 921 such that implementations of communication management module (CMM) having determination and communication capabilities may be provided as described herein. For example, apparatus described in the present disclosure may comprise all or a portion of computing device 900 and be capable of performing all or a portion of application 922 such that facilitating various types of communication between the WMD the remote device regarding the WMD and/or various data about the person wearing the WMD (e.g., physiological information) as described herein. This described basic configuration is illustrated in FIG. 9 by those components within dashed line 901.

Computing device 900 may have additional features or functionality, and additional interfaces to facilitate communications between the basic configuration 901 and any required devices and interfaces. For example, a bus/interface controller 940 may be used to facilitate communications between the basic configuration 901 and one or more data storage devices 950 via a storage interface bus 941. The data storage devices 950 may be removable storage devices 951, non-removable storage devices 952, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 920, removable storage 951 and non-removable storage 952 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of device 900.

Computing device 900 may also include an interface bus 942 for facilitating communication from various interface devices (e.g., output interfaces, peripheral interfaces, and communication interfaces) to the basic configuration 901 via the bus/interface controller 940. Example output interfaces 960 may include a graphics processing unit 961 and an audio processing unit 962, which may be configured to communicate to various external devices such as a display or speakers via one or more A/V ports 963. Example peripheral interfaces 960 may include a serial interface controller 971 or a parallel interface controller 972, which may be configured to communicate with external devices such as input devices (e.g., keyboard, mouse, pen, voice input device, touch input device, etc.) or other peripheral devices (e.g., printer, scanner, etc.) via one or more I/O ports 973. An example communication interface 980 includes a network controller 981, which may be arranged to facilitate communications with one or more other computing devices 990 over a network communication via one or more communication ports 982. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 900 may also be implemented as a personal computer including both laptop computer and non-laptop computer configurations. In addition, computing device 900 may be implemented as part of a wireless base station or other wireless system or device.

Figure 10:
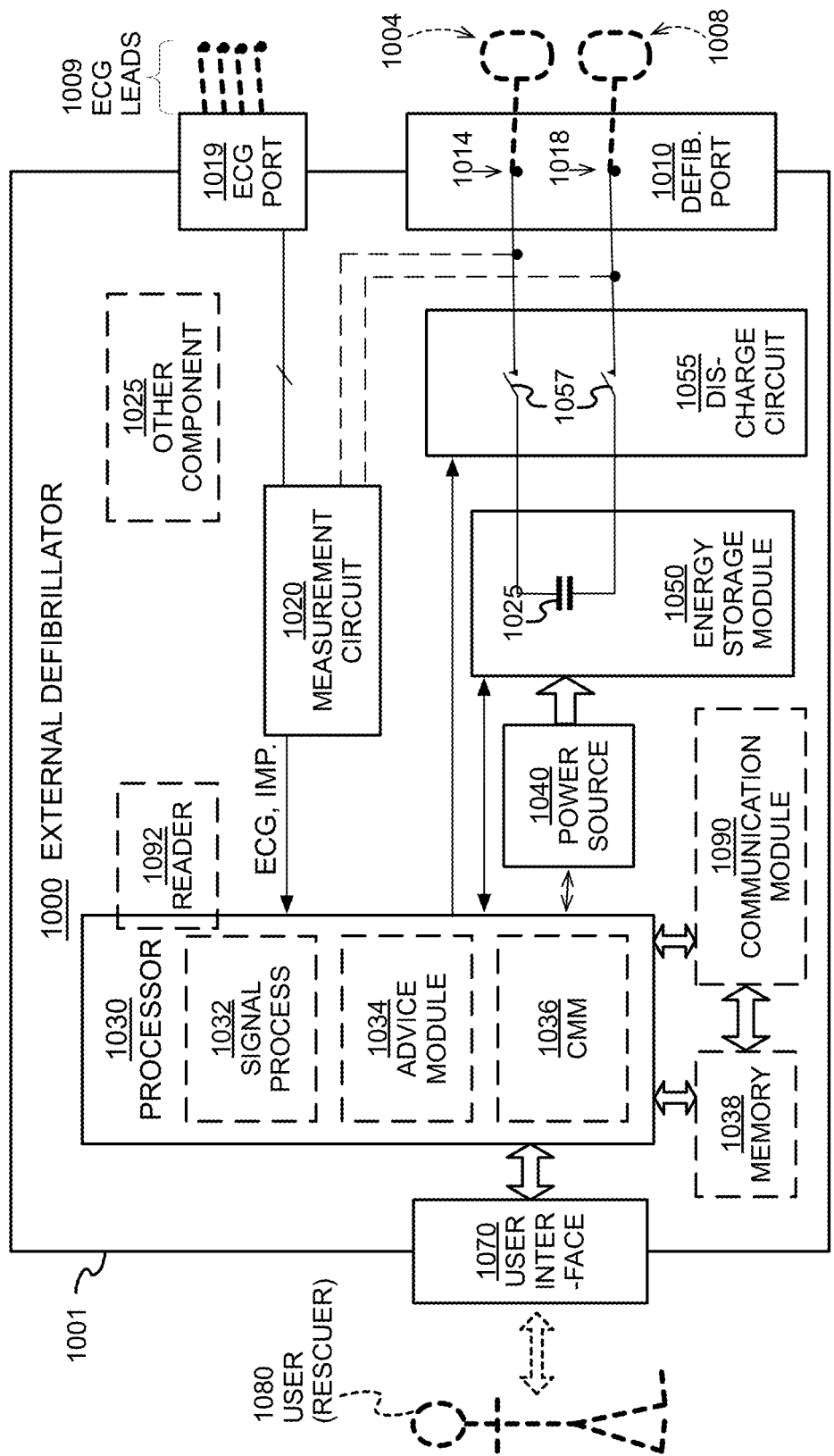
FIG. 10 is a block diagram illustrating components of a medical device, which may be used with various embodiments.

FIG. 10 is a block diagram illustrating components of a medical device (e.g., External Defibrillator 1000), which may be used with various embodiments. These components may be, for example, a medical device 102, 600, 700, and 800 (shown in FIGS. 1, 6, 7, and 8). For simplicity, the medical device may be an example of a defibrillator device.

The defibrillator device 1000 may be intended for use by a user 1080 (e.g., the person 104 and 602 shown in FIGS. 1 and 6). The defibrillator device 1000 may typically include a defibrillation port 1010, such as a socket in housing 1001. The defibrillation port 1010 may include nodes 1014 and 1018. One or more electrodes 1004 and 1008 may be plugged in to the defibrillation port 1010, so as to make electrical contact with nodes 1014 and 1018, respectively. It may also be possible that the electrodes 1004 and 1008 may be connected continuously to the defibrillation port 1010, etc. Either way, the defibrillation port 1010 may be used for guiding via the electrodes 1004 and 1008 to the person 1080 an electrical charge that may have been stored in the defibrillator device 1000, as described herein.

If the defibrillator device 1000 comprise of a heart monitoring component, as was described herein, the defibrillator device 1000 may also have an ECG port 1019 in the housing 1001, for receiving ECG leads 1009. The ECG leads 1009 may facilitate sensing of an ECG signal (e.g., a 12-lead signal or from a different number of lead signals), and electrode attachment integrity may be determined from the ECG signal, in accordance with the various embodiments disclosed herein. Moreover, a heart monitoring component could have additional ports (not shown), and the other component 1025 may be configured to utilize the electrical signal (e.g., ECG signal, impedance, etc. to facilitate determination of electrode leads off from the skin of the user 1080), in accordance with various embodiments.

The defibrillator 1000 also may include a measurement circuit 1020. The measurement circuit 1020 may receive physiological signals from the ECG port 1019, and also from other ports, if provided (e.g., previously described lead-off circuitry). The circuit 1020 may render detected physiological signals and their corresponding information. The information may be in the form of data, or other signals, etc.

The measurement circuit 1020 may obtain physiological signals through the nodes 1014 and 1018 instead, when the electrodes 1004 and 1008 are attached to the person 1080 (i.e., the skin). In these cases, a person's ECG signal may be detected as a voltage difference between the electrodes 1004 and 1008. Additionally, the impedance between the electrodes 1004 and 1008 may detect, among other things, whether the electrodes 1004 and 1008 have been inadvertently disconnected from the skin of the person 1080.

The defibrillator 1000 may also include a processor 1030. The processor 1030 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 1030 may include a number of modules. One example module may be a signal processing module 1032, which may detect outputs from the measurement circuit 1020. The signal processing module 1032 may include electronic components configured to a establish communication link between the WMD and the remote device, where the established communication may facilitate on-demand data, programing, etc. between the WMD and the remote device as described above. Accordingly, on-demand streaming data, secure remote programming, process may be facilitated in accordance with one or more embodiments.

In another example, advice module 1034 may provide advice based, at least in part, on outputs of signal processing module 1032. The advice module 1034 may include an algorithm such as, but not limited to, Shock Advisory Algorithm, implement decision rules, and so on. For example, the advice may be to shock, to not shock, to administer other forms of therapy, provide an indication to confirm a health status of the person 1080 (e.g., determine whether the person 1080 is experiencing perfusing or non-perfusing ventricular tachycardia (VT), and so on. If the advice is to shock, some defibrillator examples may report the advice to the user and prompt them to do it. In other examples, the defibrillator device may execute the advice by administering the shock. If the advice is to administer CPR, the defibrillator 1000 may further issue prompts for administrating CPR, and so forth. Examples of Shock Advisory Algorithm may be found in US patent application U.S. Ser. No. 15/421,165, filed Jan. 31, 2017 (now issued as U.S. Pat. No. 10,016,614) titled Wearable cardioverter defibrillator (WCD) system making shock/no shock determinations by aggregating aspects of multiple patient parameters, which is incorporated by reference in its entirety for all purposes.

The processor 1030 may include additional modules, such as module 1036 for various other functions such as, but not limited to, communication management module (CMM) 1036, as described herein.

In an example, the defibrillator device 1000 may include a memory 1038, which may work together with the processor 1030. The memory 1038 may be implemented in a wide variety of manners. For example, the memory 1038 may be implemented such as, but not limited to, nonvolatile memories (NVM), read-only memories (ROM), random access memories (RAM), and so forth or any combination thereof. The memory 1038 may include programs for the processor 1030, and so on. For example, the memory 1038 may include ECG signals for determining a respiration rate post-event. The programs may include operational programs executed by the processor 1030 and may also include protocols and methodologies so that decisions may be made by advice module 1034. Additionally, the memory 1038 may store various prompts for the user 1080, etc. Moreover, the memory 1038 may store a wide variety of information (i.e., predetermined parameter data) such as, but not limited to information regarding the person 1080.

The defibrillator 1000 may also include a power source 1040. In order to facilitate portability of defibrillator device 1000, the power source 1040 may include a battery type device. A battery type device may be implemented as a battery pack, which may be rechargeable or not-rechargeable. At times, a combination of rechargeable and non-rechargeable battery packs may be utilized. Examples of power source 1040 may include AC power override, where AC power may be available, and so on. In some examples, the processor 1030 may control the power source 1040.

Additionally, the defibrillator device 1000 may include an energy storage module 1050. The energy storage module 1050 may be configured to store some electrical energy (e.g., when preparing for sudden discharge to administer a shock). The energy storage module 1050 may be charged from the power source 1040 to an appropriate level of energy, as may be controlled by the processor 1030. In some implementations, the energy storage module 1050 may include one or more capacitors 1052, and the like.

The defibrillator 1000 may include a discharge circuit 1055. The discharge circuit 1055 may be controlled to facilitate discharging of the energy stored in energy storage module 1050 to the nodes 1014 and 1018. The discharge circuit 1055 may include one or more switches 1057. The one or more switches 1057 may be configured in a number of manners such as, but not limited to, an H-bridge, and so forth.

The defibrillator device 1000 may further include a user interface 1070 for the user 1080. The user interface 1070 may be implemented in a variety of manners. For example, the user interface 1070 may include a display screen capable of displaying what is detected and measured, provide visual feedback to the user 1080 for their resuscitation attempts, and so forth. The user interface 1070 may also include an audio output such as, but not limited to, a speaker to issue audio prompts, etc. The user interface 1070 may additionally include various control devices such as, but not limited to, pushbuttons, keyboards, switches, track pads, and so forth. Additionally, the discharge circuit 1055 may be controlled by the processor 1030 or directly by the user 1080 via the user interface 1070, and so forth.

Additionally, the defibrillator device 1000 may include other components. For example, a communication module 1090 may be provided for transmitting ECG signals stored on the defibrillator device 1000 to be downloaded and processed as described above. Such communication may be performed wirelessly, or via wire, or by infrared communication, near field communication (NFC), Bluetooth, WiFi, and so forth. Accordingly, information may be communicated, such as person data, incident information, therapy attempted, CPR performance, ECG information, and so forth.

A feature of a defibrillator device may be CPR related prompting. CPR prompts may be issued to the user 1080 visually or by audio facilitating assistance in the administration of CPR by the user 1080. Examples may be found in U.S. Pat. Nos. 6,334,070 and 6,356,785.

It should be appreciated after review of this disclosure that it is contemplated within the scope and spirit of the present disclosure that the claimed subject matter may include a wide variety of healthcare devices. Accordingly, the claimed subject matter is not limited in these respects.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussion utilizing terms such as "processing," "computing," "calculating," "determining" or the like refer to actions or processes of a computing device that manipulates or transforms data represented as physical electronic or magnetic quantities within memories, registers, or other information storage devices, transmission devices, or display devices of the computing device.

Claimed subject matter is not limited in scope to the particular implementations described herein. For example, some implementations may be in hardware, such as those employed to operate on a device or combination of devices, for example, whereas other implementations may be in software and/or firmware. Likewise, although claimed subject matter is not limited in scope in this respect, some implementations may include one or more articles, such as a signal bearing medium, a storage medium and/or storage media. This storage media, such as CD-ROMs, computer disks, flash memory, or the like, for example, may have instructions stored thereon that, when executed by a computing device such as a computing system, computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skilled in the art in light of this disclosure. In addition, those skilled in the art will appreciate that the mechanisms of the subject matter described herein are capable of being distributed as a product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. A wearable medical device system, comprising:
   a remote device;
   a wearable medical device (WMD); and
   a communication management module (CMM) communicatively coupled with the remote device and the WMD, the CMM configured to:
     establish a communication link between the remote device and the WMD,
     communicate first data from the WMD to the remote device using the communication link, wherein the first data includes an event detected by the WMD,
     responsive to the communicated first data, communicate a request for second data from the remote device to the WMD using the communication link, wherein the request for the second data is based upon content of the communicated first data, and
     responsive to the request for the second data, communicate the second data from the WMD to the remote device using the communication link, wherein the second data includes additional data related to the event.

2. The wearable medical device system of claim 1, further comprising a communication device, the communication device configured to host the CMM.

3. The wearable medical device system of claim 2, wherein the communication device comprises a smartphone.

4. The wearable medical device system of claim 1, wherein the remote device comprises a medical professional device.

5. The wearable medical device system of claim 1, wherein the communication link comprises an Internet based communication link.

6. The wearable medical device system of claim 1, wherein the WMD comprises a wearable cardioverter defibrillator (WCD).

7. The wearable medical device system of claim 1, wherein the WMD comprises an alarm configured to be activated by a user of the WMD, and wherein the event detected by the WMD further corresponds to the alarm activated by the user.

8. The wearable medical device system of claim 1, wherein the event detected by the WMD further corresponds to a specified duration of wear time of the WMD.

9. A wearable medical device system, comprising:
a remote device;
a wearable medical device (WMD) comprising one or more components; and
a communication management module (CMM) communicatively coupled with the remote device and the WMD, the CMM configured to:
  establish a communication link between the remote device and the WMD,
  communicate first data from the WMD to the remote device using the communication link, wherein the first data includes identification data of at least one component, of the one or more components of the WMD, which is replaced or modified,
  responsive to the communicated first data, communicate a request for second data from the remote device to the WMD using the communication link, wherein the request for the second data is based upon content of the communicated first data, and
  responsive to the request for the second data, communicate the second data from the WMD to the remote device using the communication link, wherein the second data includes additional information of the replaced or modified at least one component.

10. The wearable medical device system of claim 9, further comprising a communication device, the communication device configured to host the CMM.

11. The wearable medical device system of claim 10, wherein the communication device comprises a smartphone.

12. The wearable medical device system of claim 9, wherein the remote device comprises a medical professional device.

13. The wearable medical device system of claim 9, wherein the communication link comprises an Internet based communication link.

14. The wearable medical device system of claim 9, wherein the WMD comprises a wearable cardioverter defibrillator (WCD).

15. A wearable medical device system, comprising:
a remote device;
a wearable medical device (WMD); and
a communication management module (CMM) communicatively coupled with the remote device and the WMD, the CMM configured to:
  establish a communication link between the remote device and the WMD,
  receive a request to program the WMD from the remote device,
  upon receiving the request to program the WMD, receive a programming authentication from the remote device authorizing the CMM to program the WMD, and
  upon receiving the programming authentication from the remote device, remotely program the WMD in a secure manner using the communication link.

16. The wearable medical device system of claim 15, further comprising a communication device, the communication device configured to host the CMM.

17. The wearable medical device system of claim 16, wherein the communication device comprises a smartphone.

18. The wearable medical device system of claim 15, wherein the remote device comprises a medical professional device.

19. The wearable medical device system of claim 15, wherein the communication link comprises an Internet based communication link.

20. The wearable medical device system of claim 15, wherein the WMD comprises a wearable cardioverter defibrillator (WCD).

* * * * *